(12) United States Patent
Cohen et al.

(10) Patent No.: US 11,523,872 B1
(45) Date of Patent: Dec. 13, 2022

(54) SYSTEMS AND METHODS FOR GUIDING MANIPULATION OF ENDOSCOPIC TOOLS FOR ENDOSCOPIC SURGERY

(71) Applicant: Memic Innovative Surgery Ltd., Or-Yehuda (IL)

(72) Inventors: Dvir Cohen, Ramot-Menashe (IL); Yaron Levinson, Tel-Aviv (IL)

(73) Assignee: Memic Innovative Surgery Ltd., Or-Yehuda (IL)

( * ) Notice: Subject to any disclaimer, the term of this patent is extended or adjusted under 35 U.S.C. 154(b) by 561 days.

(21) Appl. No.: 16/701,187

(22) Filed: Dec. 3, 2019

Related U.S. Application Data

(60) Provisional application No. 62/774,364, filed on Dec. 3, 2018.

(51) Int. Cl.
| | | |
|---|---|---|
| *A61B 34/00* | (2016.01) | |
| *A61B 1/00* | (2006.01) | |
| *A61B 90/92* | (2016.01) | |
| *A61B 1/303* | (2006.01) | |
| *A61B 17/00* | (2006.01) | |
| *A61B 34/30* | (2016.01) | |
| *A61B 90/00* | (2016.01) | |

(52) U.S. Cl.
CPC .......... *A61B 34/25* (2016.02); *A61B 1/00045* (2013.01); *A61B 1/303* (2013.01); *A61B 17/00234* (2013.01); *A61B 34/76* (2016.02); *A61B 90/92* (2016.02); *A61B 2017/00119* (2013.01); *A61B 2034/256* (2016.02); *A61B 2034/302* (2016.02); *A61B 2034/742* (2016.02); *A61B 2090/374* (2016.02); *A61B 2090/378* (2016.02); *A61B 2090/3762* (2016.02)

(58) Field of Classification Search
CPC ..................................................... A61B 34/25
See application file for complete search history.

(56) References Cited

U.S. PATENT DOCUMENTS

| | | | | |
|---|---|---|---|---|
| 9,192,392 B2* | 11/2015 | van der Walt | ..... | A61B 17/7017 |
| 2002/0077540 A1* | 6/2002 | Kienzle, III | ....... | A61B 17/1703 |
| | | | | 606/130 |
| 2003/0069591 A1* | 4/2003 | Carson | ................. | A61B 17/154 |
| | | | | 606/130 |
| 2006/0142657 A1* | 6/2006 | Quaid | ................ | A61B 17/1703 |
| | | | | 600/424 |
| 2019/0380792 A1* | 12/2019 | Poltaretskyi | ........... | A61B 34/25 |

* cited by examiner

*Primary Examiner* — Christian A Sevilla

(57) ABSTRACT

There is provided a computer implemented method of providing a surgical controller with instructions to restrict a manipulation of an endoscopic tool during an endoscopic medical procedure in an intrabody cavity, comprising: inputting into classifier(s), indication(s) of instructions for manipulation of the endoscopic tool outputted by sensor(s), classifying by the classifier(s), the indication of instructions into an envelope defining a volume that restricts therein manipulation of the endoscopic tool, wherein the classifier(s) classifies the envelope based on previously obtained indications of instructions for manipulation of endoscopic tools during other endoscopic medical procedures performed in intrabody cavities of other patients, analyzing the indication of instructions for manipulation of the endoscopic tool according to the envelope to determine when the instructions are for manipulation of the endoscopic tool externally to the envelope, and providing the surgical controller with an indication of inappropriate manipulation according to the analysis.

45 Claims, 4 Drawing Sheets

SYSTEMS AND METHODS FOR GUIDING MANIPULATION OF ENDOSCOPIC TOOLS FOR ENDOSCOPIC SURGERY

RELATED APPLICATION(S)

This application claims the benefit of priority under 35 USC § 119(e) of U.S. Provisional Patent Application No. 62/774,364 filed on Dec. 3, 2018, the contents of which are incorporated by reference as if fully set forth herein in their entirety.

FIELD AND BACKGROUND OF THE INVENTION

The present invention, in some embodiments thereof, relates to endoscopic tools and, more specifically, but not exclusively, to systems and methods for guiding manipulation of endoscopic tools for performing endoscopic surgery.

Different systems and methods have been created for assisting physicians in performing endoscopic surgery in a patient using endoscopic tools. Endoscopic surgery is unlike traditional surgery, in which the operating physician handholds the tools and is able to directly feel the tool during the procedure and directly control the forces applied to the tools, while directly visually observing the field of surgery. In endoscopic surgery, the operating physician performs procedures remotely, by indirectly and remotely maneuvering endoscopic tools located inside the body by a controller located outside the body. The operating physician indirectly views the operating field via images captured by a camera inside the body that are presented on a screen located outside the body.

SUMMARY OF THE INVENTION

According to a first aspect, a computer implemented method of providing a surgical controller with instructions to restrict a manipulation of an endoscopic tool during an endoscopic medical procedure in an intrabody cavity, comprises: inputting into at least one classifier, at least one indication of instructions for manipulation of the endoscopic tool outputted by at least one sensor, classifying by the at least one classifier, the indication of instructions into an envelope defining a volume that restricts therein manipulation of the endoscopic tool, wherein the at least one classifier classifies the envelope based on previously obtained indications of instructions for manipulation of endoscopic tools during other endoscopic medical procedures performed in intrabody cavities of other patients, analyzing the indication of instructions for manipulation of the endoscopic tool according to the envelope to determine when the instructions are for manipulation of the endoscopic tool externally to the envelop, and providing the surgical controller with an indication of inappropriate manipulation according to the analysis.

According to a second aspect, a computer implemented method of training at least one classifier to classify an indication of instructions for manipulation of endoscopic tool during an endoscopic medical procedure in an intrabody cavity, the method comprises: receiving for each of a plurality of endoscopic procedures, at least one indication of instructions for manipulation of the endoscopic tool outputted by at least one sensor, computing a plurality of training envelopes according to the at least one indication of instructions for manipulation of the endoscopic tool for the plurality of endoscopic procedures, wherein each training envelope of the plurality of training envelopes defines a respective volume denoting restricted manipulation of the endoscopic tool therein, and training at least one classifier according to the plurality of training envelopes and the at least one indication of instructions for manipulation of the plurality of endoscopic tools, to classify a new envelope for a new indication of instructions for manipulation of an endoscopic tool during a new endoscopic procedure.

According to a third aspect, a system for providing a surgical controller with instructions to restrict a manipulation of an endoscopic tool during an endoscopic medical procedure in an intrabody cavity, comprises: a non-transitory memory having stored thereon a code for execution by at least one hardware processor, the code comprising: code for inputting into at least one classifier, at least one indication of instructions for manipulation of the endoscopic tool outputted by at least one sensor, code for classifying by at least one classifier, the indication of instructions into an envelope defining a volume that restricts therein manipulation of the endoscopic tool, wherein the at least one classifier classifies the envelope based on previously obtained indications of instructions for manipulation of endoscopic tools during other endoscopic medical procedures performed in intrabody cavities of other patients, code for analyzing the indication of instructions for manipulation of the endoscopic tool according to the envelope to determine when the instructions are for manipulation of the endoscopic tool externally to the envelop, and code for providing the surgical controller with an indication of inappropriate manipulation according to the analysis.

At least some of the systems, apparatus, methods and/or code instructions described herein improve the medical field of endoscopic surgery using endoscopic tools, by reducing the risk of damage occurring to a patient resulting from inappropriate manipulation of the endoscopic tool. The computed envelope described herein is used to detect an indication of inappropriate manipulation of the endoscopic tool, before the instructions for manipulation of the tool are implemented by a surgical controller. The surgical controller may prevent the inappropriate manipulation of the endoscopic tool from occurring by preventing execution of the instructions of the endoscopic tool, preventing harm to the patient.

At least some of the systems, apparatus, methods and/or code instructions described herein address the technical problem of preventing and/or reducing injury occurring to a patient due to errors and/or improper in manipulation of endoscopic tools within an intrabody cavity of the patient. For example, errors in manipulation may injure tissue of the patient by exertion of a physical force by the endoscopic tool, and/or improper manipulation may result in excess bleeding and/or incomplete removal of target tissue.

At least some of the systems, apparatus, methods and/or code instructions described herein address the technical problem of improving ergonomic positioning of an operator of an endoscopic tool during an endoscopic procedure. Operators ergonomically positioned during the procedure may perform the endoscopic procedure with relatively reduced time and/or relatively reduced errors, for example, due to decreased fatigue and/or increased comfort, in comparison to performing the procedure in an ergonomically poor position.

At least some of the systems, apparatus, methods and/or code instructions described herein learn from best practice manipulations performed by other physicians, to guide the current user into performing similar manipulations based on the best practice manipulations. The computed envelope may represent a restriction zone where the majority or all of the other physicians performed manipulations of endoscopic tools, conceptually defining the best practice restriction zone. Manipulation of the endoscopic tools externally to the envelope represents uncommon behavior that does not meet best practices, and which is therefore to be prevented due to a high risk of injury to the patient and/or due to poor ergonomic positioning of the operator. The behavior in terms of manipulation of the endoscopic tools observed in other physicians that performed similar endoscopic procedures is consolidated into a best practice, defined by the envelope which represents an aggregation of the best practice manipulation performed by the other physicians. Users that attempt to deviate from the envelope are performing a manipulation that is uncommon and/or does not conform to the best practice of their peers.

At least some of the systems, apparatus, methods and/or code instructions described herein are directed to an improvement in computer-related technology, by allowing computers to compute an envelope that restricts manipulation of an endoscopic tool therein. Such envelope is directly tied to computer technology. For example, previously physicians were trained by direct observation of their peers, to make sure that the manipulations performed by the operator were conforming to best surgical practice and/or were not risking damage to the patient. Such operators had to rely on other methods, for example, slowing down manipulations performed during the procedure to be certain that the manipulation is safe and/or effective, previous training, gut instinct, an educated guess, and/or direct observation by colleagues and/or supervisors. However, it is noted that the systems, apparatus, methods and/or code instructions described herein are not a computer-implemented version of a mental process, and are not intended to replicate or model human capability, but provide an improvement in the ability to analyze a large number of instructions for manipulations of endoscopic tools for computation of the envelope that restricts manipulation of the endoscopic tool therein. Such virtual envelope is directly tied to computer technology.

In a further implementation form of the first, second, and third aspects, the endoscopic procedure is performed by introducing the endoscopic tools into an abdominal cavity of the patient via transvaginal access.

In a further implementation form of the first, second, and third aspects, the envelope is defined in four dimensions, including dynamically defining the volume over a time interval.

In a further implementation form of the first, second, and third aspects, the at least one classifier comprise a dynamic classifier that computes dynamic adaptations of the volume over the time interval.

In a further implementation form of the first, second, and third aspects, the dynamic classifier is implemented as a Markov Chain.

In a further implementation form of the first, second, and third aspects, the envelope is dynamically classified by the at least one classifier as the instructions for manipulation of the endoscopic tool are dynamically outputted by the at least one sensor during the endoscopic procedure.

In a further implementation form of the first, second, and third aspects, the method further comprises and/or the system further comprises code for providing haptic feedback to a haptic device manipulated by a user for manipulating the endoscopic tool, the haptic feedback generated according to the indication of inappropriate manipulation.

In a further implementation form of the first, second, and third aspects, the haptic feedback comprises resistance to movement of the haptic device when the haptic device is manipulated for manipulation of the endoscopic tool externally to the envelope.

In a further implementation form of the first, second, and third aspects, the method further comprises and/or the system further comprises code for providing haptic feedback to a haptic device manipulated by a user for manipulating the endoscopic tool, the haptic feedback comprising a resistance force proportional to a vector from a current position of the endoscopic tool to the envelope.

In a further implementation form of the first, second, and third aspects, the envelope is classified according to the instructions for manipulation of the endoscopic tool relative to an initial position and orientation of the endoscopic tool.

In a further implementation form of the first, second, and third aspects, the envelope is classified according to a history of previous manipulations of the endoscopic tool.

In a further implementation form of the first, second, and third aspects, the surgical controller is provided with the indication of inappropriate manipulation prior to the surgical controller activating the endoscopic tool for implementing the instructions for manipulation of the endoscopic tool.

In a further implementation form of the first, second, and third aspects, the volume defined by the envelope is computed according to a threshold of the previously obtained indications of instructions for manipulation of endoscopic tools during other endoscopic medical procedures performed in intrabody cavities of other patients.

In a further implementation form of the first, second, and third aspects, the threshold differentiates between common manipulations indicative of allowed manipulations and uncommon manipulations indicative of prohibited manipulations.

In a further implementation form of the first, second, and third aspects, the envelope comprise a plurality of nested sub-volumes, each respective nested sub-volume indicative of a respective proportion according to a respective threshold of the previously obtained indications of instructions for manipulation of endoscopic tools during other endoscopic medical procedures performed in intrabody cavities of other patients.

In a further implementation form of the first, second, and third aspects, the respective proportion of the respective nested sub-volume is indicative of a probability of manipulations being allowed within the respective nested sub-volume.

In a further implementation form of the first, second, and third aspects, each of a plurality of different indications of inappropriate manipulations is generated according to an analysis indicative of a distance from the envelope to the endoscopic tool when manipulated according to the instructions for manipulation.

In a further implementation form of the first, second, and third aspects, the plurality of different indications of inappropriate manipulations are indicative of increasing risk of injury to the patient when the endoscopic tool is manipulated within the respective sub-volume.

In a further implementation form of the first, second, and third aspects, the envelope comprises a probability density cloud, wherein sub-volumes of the envelope are each associated with a respective probability value indicative of manipulations being allowed within the respective sub-volume, wherein each probability is computed according to a ratio between previously performed manipulations within the sub-volume and total performed manipulations.

In a further implementation form of the first, second, and third aspects, the envelope comprises a plurality of sub-envelopes each defining restriction of movement of a respective independently bendable flexible section of the endoscopic tool.

In a further implementation form of the first, second, and third aspects, an indication of the envelope is marked on an image presented on a display, the image is at least one of: captured by a video camera located within the target individual, captured by an anatomical imaging modality imaging the target individual, and an anatomical image obtained from an atlas.

In a further implementation form of the first, second, and third aspects, the envelope dynamically changes colors according to a distance between a current location of the endoscopic tool and the envelope, the color indicative of the amount of the distance.

In a further implementation form of the first, second, and third aspects, the indication of inappropriate manipulation is presented on a display.

In a further implementation form of the first, second, and third aspects, the method further comprises and/or the system further comprises code for receiving a profile of the target individual and classifying the envelope by the at least one classifier according to an analysis of profiles of other patients correlated with the profile of the target individual.

In a further implementation form of the first, second, and third aspects, the profile of the target individual and the profiles of other patients include at least one parameter selected from the group consisting of: gender, age, weight, body mass index (BMI), previous surgeries, anatomical variations, and medical history.

In a further implementation form of the first, second, and third aspects, the method further comprises and/or the system further comprises code for receiving a hardware profile of the endoscopic tool and classifying the envelope by the at least one classifier according to an analysis of hardware profiles of endoscopic tools used during other endoscopic medical procedures correlated with the hardware profile.

In a further implementation form of the first, second, and third aspects, the hardware profile of the endoscopic tool and the hardware profiles of endoscopic tools used during other endoscopic medical procedures include at least one parameter selected from the group consisting of: tool manufacturer, tool model, tool intended use, length of tool, range of movement, range of force application, and tool architecture.

In a further implementation form of the first, second, and third aspects, the method further comprises and/or the system further comprises code for receiving a procedure profile of the endoscopic procedure and classifying the envelope by the at least one classifier according to an analysis of procedure profiles of other endoscopic procedures correlated with the procedure profile.

In a further implementation form of the first, second, and third aspects, the procedure profile of the endoscopic procedure and the procedure profiles of other endoscopic procedures include at least one parameter selected from the group consisting of: type of endoscopic procedure, planned route of endoscopic procedure, location of access port(s) into the body of the target individual.

In a further implementation form of the first, second, and third aspects, the surgical controller comprises the at least one sensor that receives manipulation instructions from a haptic device manipulated by a user for activating at least one motor that controls the endoscopic tool.

In a further implementation form of the first, second, and third aspects, the at least one sensor comprises a computing device that monitors activation of motors that control the endoscopic tool.

In a further implementation form of the first, second, and third aspects, the at least one sensor comprises a current measuring sensor that senses current flowing through at least one motor that control the endoscopic tool, wherein the current is indicative of at least one of stress and torque experienced by the endoscopic tool during manipulation.

In a further implementation form of the first, second, and third aspects, the instructions for manipulation include a movement from a current position of the endoscopic tool.

In a further implementation form of the first, second, and third aspects, the method further comprises and/or the system further comprises code for computing a recommendation for an alternative manipulation that remains within the volume defined by the envelope.

In a further implementation form of the first, second, and third aspects, the alternative manipulation is computed in comparison to the instructions for manipulation of the endoscopic tool according to at least one of: a predicted reduction in strain within the endoscopic tool, a predicted reduction in radius of curvature of a portion of the endoscopic tool, and a predicted reduction in distance to tissue located externally to the envelope.

In a further implementation form of the first, second, and third aspects, the method further comprises and/or the system further comprises code for analyzing the instructions for manipulation of the endoscopic tool to identify an ergonomically poor posture of the operator, and wherein the alternative manipulation is computed according to manipulation of the endoscopic tool based on an ergonomic easing of the operator.

In a further implementation form of the first, second, and third aspects, the alternative manipulation is computed as an alternative angle for performing a dissection using the endoscopic tool.

In a further implementation form of the first, second, and third aspects, the alternative manipulation is computed by subtracting 180 degrees from the current bending angle of the endoscopic tool.

In a further implementation form of the first, second, and third aspects, the at least one classifier is trained according to endoscopic procedures performed by operators instructed for ergonomically easy manipulation of the endoscopic tool, wherein the envelope denotes a volume including possible ergonomically easy manipulations.

In a further implementation form of the first, second, and third aspects, the instructions for manipulation include at least one of: angle of movement at a joint, and in-out motion relative to an insertion port.

In a further implementation form of the second aspect, each one of the plurality of training envelopes is computed for a certain position and orientation of the endoscopic tool according to a volume that encompasses a plurality of manipulations performed relative to the certain position and orientation during the plurality of endoscopic procedures.

In a further implementation form of the second aspect, outlier manipulations of the plurality of manipulations satisfying outlier criteria are excluded for computation of the respective envelope.

In a further implementation form of the second aspect, the method further comprises receiving a plurality of prohibited indications each of a prohibited manipulation of the respective endoscopic tool, wherein the plurality of training envelopes are computed according to the prohibited indications, wherein the volumes of the plurality of training envelopes exclude the prohibited manipulations and the prohibited manipulates are located externally to the plurality of envelopes.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1:
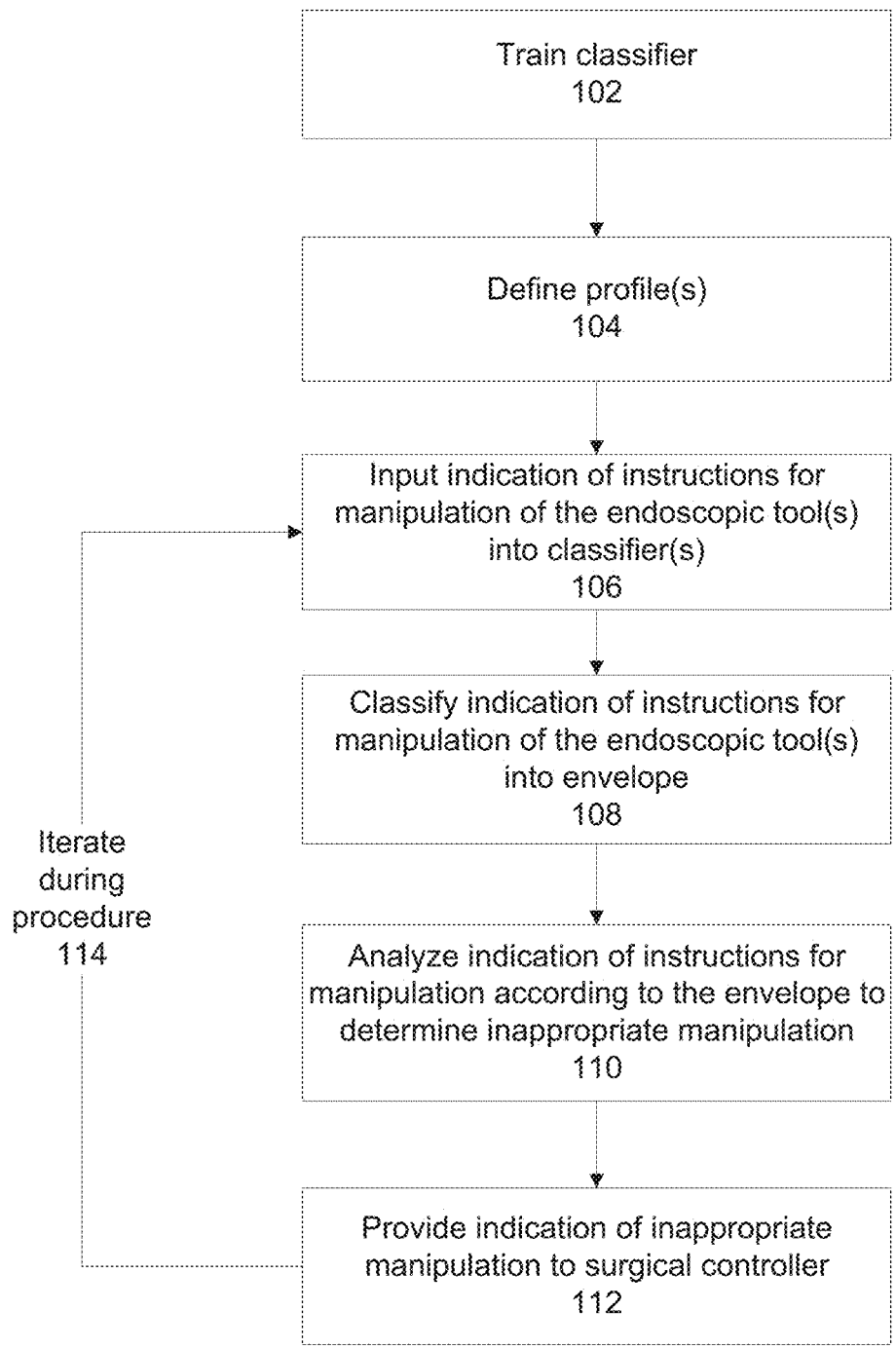
FIG. 1 is a flowchart of a method of providing a surgical controller with instructions to restrict a manipulation of an endoscopic tool during an endoscopic medical procedure in an intrabody cavity, in accordance with some embodiments of the present invention.

The present invention, in some embodiments thereof, relates to endoscopic tools and, more specifically, but not exclusively, to systems and methods for guiding manipulation of endoscopic tools for performing endoscopic surgery.

An aspect of some embodiments of the present invention relates to systems, an apparatus, methods, and/or code instructions (stored in a data storage device, executable by one or more hardware processors) for providing a surgical controller with instructions to restrict manipulation of an endoscopic tool(s) during an endoscopic medical procedure in an intrabody cavity, optionally transvaginal access to the abdomen which is optionally inflated with gas. One or more indications of instructions for manipulation of the endoscopic tool outputted by sensor(s) are inputted into at least one classifier. The indication of instructions for manipulation of the endoscopic tool are generated in response to a user manually manipulating a user control located outside the body of the patient. The instructions are analyzed by a surgical controller for manipulation of the endoscopic tools (e.g., robotic arms) for performing the endoscopic procedure within the intrabody cavity of the patient. The classifier(s) classify the indication of instructions into an envelope that virtually surrounds the endoscopic tool.

The envelope defines a volume that restricts manipulation of the endoscopic tool. The classifier(s) computes the envelope based on previously obtained indications of instructions for manipulation of endoscopic tools during other endoscopic medical procedures performed in intrabody cavities of other patients. Conceptually, the envelope defines a restriction zone according to best practices of other physicians performing similar procedures. The indication of instructions for manipulation of the endoscopic tool is analyzed according to the envelope to determine when the instructions are for manipulation of the endoscopic tool externally to the envelope. When the endoscopic tool is being manipulated external to the envelope, the surgical controller is provided with an indication of inappropriate manipulation. The surgical controller may prevent manipulation of the endoscopic tool outside of the envelope, for example, by increasing resistance of a haptic device acting as the user control to prevent the user from guiding the endoscopic tool externally to the envelope. The envelope is dynamically computed and/or adjusted and/or updated in real time, as the endoscopic tool is dynamically manipulated as part of the endoscopic procedure.

Optionally, the envelope is classified according to the instructions for manipulation of the endoscopic tool relative to an initial position and orientation of the endoscopic tool.

Optionally, the envelope is defined in 4 dimensions, including the volume defined over a time internal. The time interval may include the current time, a future time, and optionally a historical time. The classifier(s) computing the envelope may be implemented as a dynamic classifier that computes the envelope in four dimensions, for example, including computing an initial state of the volume of the envelope and a dynamic adaptation of the volume over a time interval from the initial state. The dynamic classifier may be implemented as, for example, a Markov Chain.

An aspect of some embodiments of the present invention relates to systems, an apparatus, methods, and/or code instructions (stored in a data storage device, executable by one or more hardware processors) for training one or more classifiers for classifying an indication of instructions for manipulation of endoscopic tool during an endoscopic medical procedure in an intrabody cavity of a patient, into an envelope. The classifier is trained based on a training dataset, which includes indications of instructions for manipulation of the endoscopic tool outputted by one or more sensor(s) that are collected during multiple endoscopic procedures performed by respective operating physicians. Multiple training envelopes may be computed, where each training envelope is computed according to one or more respective indications of instructions for manipulation of the endoscopic tool for the respective procedure, optionally relative to an initial (i.e., certain) position and/or orientation of the endoscopic tool.

The training envelope may define a volume for the respective procedure(s) that defines the extent of manipulation(s) of the endoscopic tool, optionally relative to the certain position and/or orientation. The manipulation of the endoscopic tool is restricted to the volume during the respective procedure(s). Each computed training envelope conceptually represents a best practice endoscopic tool manipulation of the respective physician(s) that performed the respective procedure(s). The classifier is trained according to the multiple computed training envelopes and corresponding indications of instructions for manipulation of the endoscopic tools, for classifying a new envelope for a new indication of instructions for manipulation of an endoscopic tool during a new endoscopic procedure.

At least some of the systems, apparatus, methods and/or code instructions described herein improve the medical field of endoscopic surgery using endoscopic tools, by reducing the risk of damage occurring to a patient resulting from inappropriate manipulation of the endoscopic tool. The computed envelope described herein is used to detect an indication of inappropriate manipulation of the endoscopic tool, before the instructions for manipulation of the tool are implemented by a surgical controller. The surgical controller may prevent the inappropriate manipulation of the endoscopic tool from occurring by preventing execution of the instructions of the endoscopic tool, preventing harm to the patient.

At least some of the systems, apparatus, methods and/or code instructions described herein address the technical problem of preventing and/or reducing injury occurring to a patient due to errors and/or improper in manipulation of endoscopic tools within an intrabody cavity of the patient. For example, errors in manipulation may injure tissue of the patient by exertion of a physical force by the endoscopic tool, and/or improper manipulation may result in excess bleeding and/or incomplete removal of target tissue.

At least some of the systems, apparatus, methods and/or code instructions described herein address the technical problem of improving ergonomic positioning of an operator of an endoscopic tool during an endoscopic procedure. Operators ergonomically positioned during the procedure may perform the endoscopic procedure with relatively reduced time and/or relatively reduced errors, for example, due to decreased fatigue and/or increased comfort, in comparison to performing the procedure in an ergonomically poor position.

At least some of the systems, apparatus, methods and/or code instructions described herein learn from best practice manipulations performed by other physicians, to guide the current user into performing similar manipulations based on the best practice manipulations. The computed envelope may represent a restriction zone where the majority or all of the other physicians performed manipulations of endoscopic tools, conceptually defining the best practice restriction zone. Manipulation of the endoscopic tools externally to the envelope represents uncommon behavior that does not meet best practices, and which is therefore to be prevented due to a high risk of injury to the patient and/or due to poor ergonomic positioning of the operator. The behavior in terms of manipulation of the endoscopic tools observed in other physicians that performed similar endoscopic procedures is consolidated into a best practice, defined by the envelope which represents an aggregation of the best practice manipulation performed by the other physicians. Users that attempt to deviate from the envelope are performing a manipulation that is uncommon and/or does not conform to the best practice of their peers.

At least some of the systems, apparatus, methods and/or code instructions described herein are directed to an improvement in computer-related technology, by allowing computers to compute an envelope that restricts manipulation of an endoscopic tool therein. Such envelope is directly tied to computer technology. For example, previously physicians were trained by direct observation of their peers, to make sure that the manipulations performed by the operator were conforming to best surgical practice and/or were not risking damage to the patient. Such operators had to rely on other methods, for example, slowing down manipulations performed during the procedure to be certain that the manipulation is safe and/or effective, previous training, gut instinct, an educated guess, and/or direct observation by colleagues and/or supervisors.

However, it is noted that the systems, apparatus, methods and/or code instructions described herein are not a computer-implemented version of a mental process, and are not intended to replicate or model human capability, but provide an improvement in the ability to analyze a large number of instructions for manipulations of endoscopic tools for computation of the envelope that restricts manipulation of the endoscopic tool therein. Such virtual envelope is directly tied to computer technology.

At least some implementations of the systems, apparatus, methods and/or code instructions described herein generate a new user experience, one that is different than the user mentally trying to determine which manipulations are safe and/or efficient. The user is able to focus on performing the procedure, while being prevented from performing unsafe and/or inefficient manipulations.

At least some implementations of the systems, apparatus, methods and/or code instructions described herein improve patient safety by reducing risk of injury from improper manipulations resulting for example, from operator error.

At least some implementations of the systems, apparatus, methods and/or code instructions described herein improve medical effectiveness of the procedure and/or reduce procedure time by increasing the efficiency of manipulations of the endoscopic tool.

At least some implementations of the systems, apparatus, methods and/or code instructions described herein improve an underlying technical process within the technical field of endoscopic surgery.

At least some implementations of the systems, apparatus, methods and/or code instructions described herein generate new data in the form of the envelope, which as described herein, has not been previously performed by a computer and has no manual counterpart.

At least some implementations of the systems, apparatus, methods and/or code instructions described herein are tied to physical real-life components, for example, the endoscopic tool(s), the surgical controller hardware that controls the endoscopic tool(s), the user control that generates instructions for manipulation of the endoscopic tool, a display that presents an image of the envelope, and the hardware processor(s) that executes code instructions, as well as the memory storage device storing the code instructions, are all physical real-life components.

At least some implementations of the systems, apparatus, methods and/or code instructions described herein provide a unique, particular, and advanced technique of controlling manipulation of endoscopic tools within an intrabody cavity of a patient during an endoscopic medical procedure.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages.

The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the term classifier may refer to one or multiple classifiers and/or artificial intelligence code. For example, multiple classifiers may be trained, which may process data in parallel and/or as a pipeline. For example, output of one type of classifier (e.g., from intermediate layers of a neural network) is fed as input into another type of classifier. Exemplary classifiers include: Markov chains, one or more neural networks of various architectures (e.g., artificial, deep, convolutional, fully connected), support vector machine (SVM), logistic regression, k-nearest neighbor, and decision trees.

Figure 2:
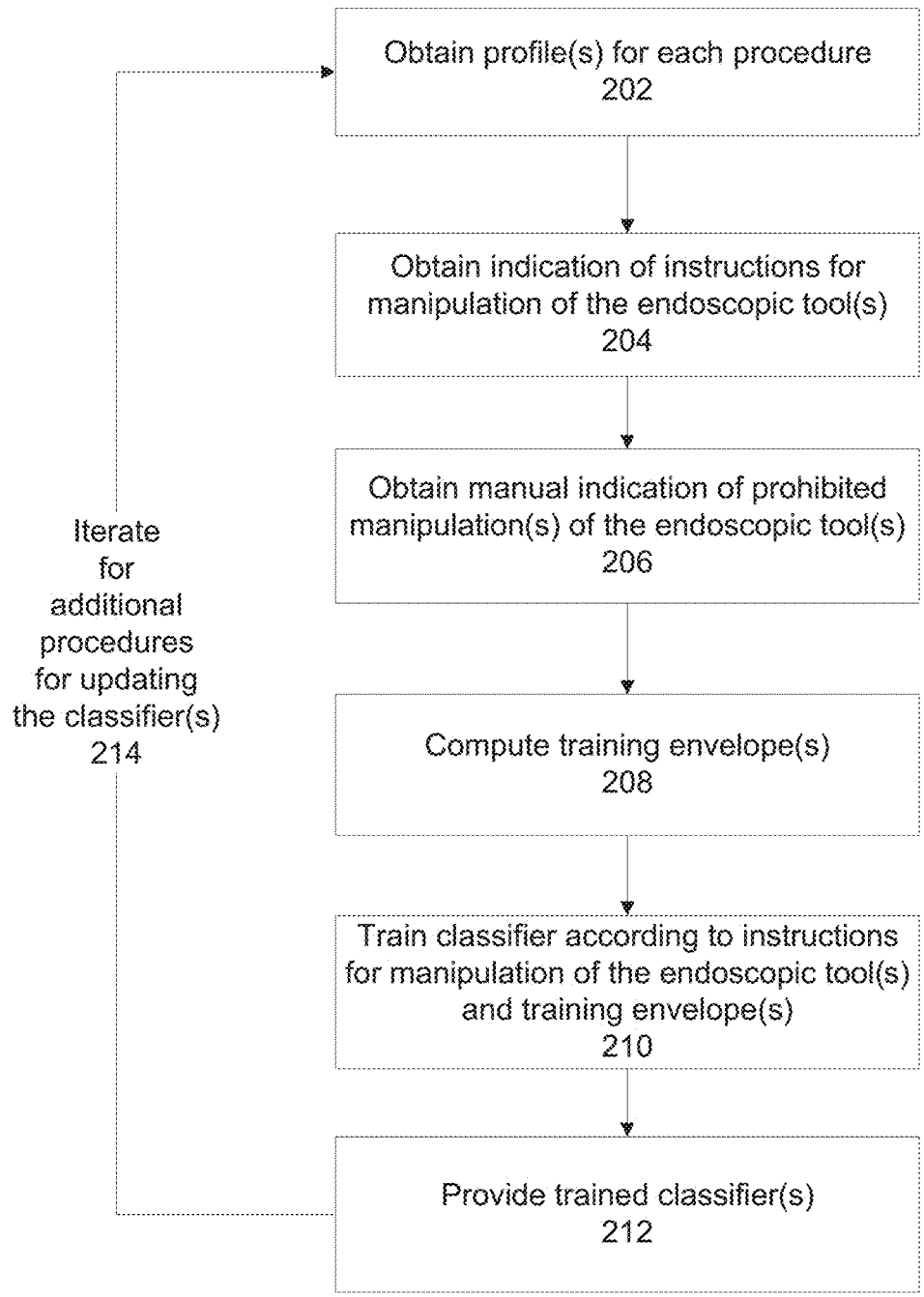
FIG. 2 is a flowchart of a method of training one or more classifiers to classify an indication of instructions for manipulation of endoscopic tool during an endoscopic medical procedure in an intrabody cavity, in accordance with some embodiments of the present invention.

Reference is now made to FIG. 1, which is a flowchart of a method of providing a surgical controller with instructions to restrict a manipulation of an endoscopic tool during an endoscopic medical procedure in an intrabody cavity, in accordance with some embodiments of the present invention. Reference is also made to FIG. 2, which is a flowchart of a method of training one or more classifiers to classify an indication of instructions for manipulation of endoscopic tool during an endoscopic medical procedure in an intrabody cavity, in accordance with some embodiments of the present invention.

Figure 3:
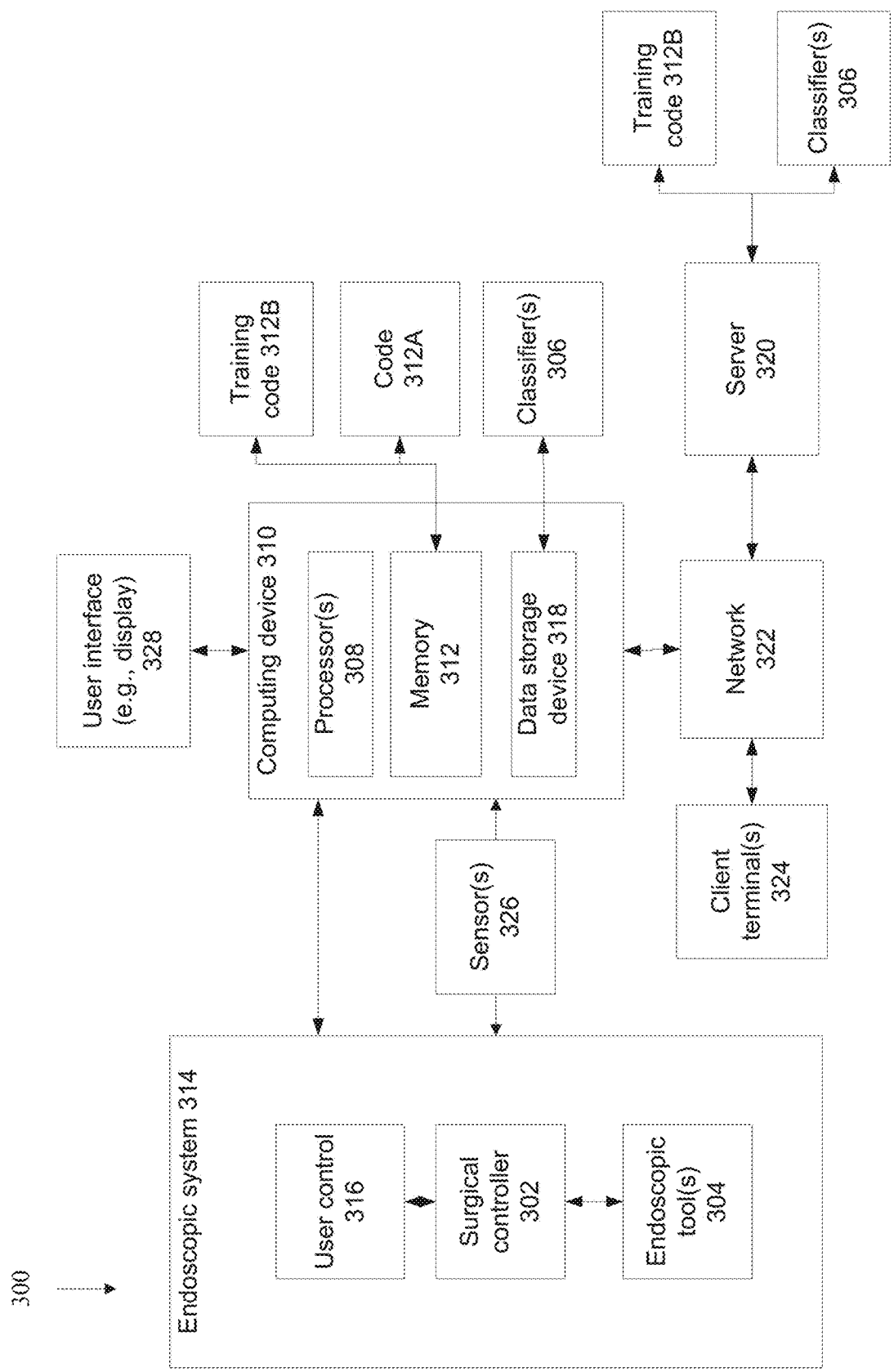
FIG. 3 is a block diagram of components of a system for providing a surgical controller with instructions to restrict a manipulation of an endoscopic tool during an endoscopic medical procedure in an intrabody cavity, and/or for training one or more classifiers to classify an indication of instructions for manipulation of endoscopic tool during an endoscopic medical procedure in an intrabody cavity, in accordance with some embodiments of the present invention.

Reference is also made to FIG. 3, which is a block diagram of components of a system 300 for providing a surgical controller 302 with instructions to restrict a manipulation of an endoscopic tool 304 during an endoscopic medical procedure in an intrabody cavity, and/or for training one or more classifiers 306 to classify an indication of instructions for manipulation of endoscopic tool 304 during an endoscopic medical procedure in an intrabody cavity, in accordance with some embodiments of the present invention. System 300 may implement the acts of the methods described with reference to FIGS. 1-2, optionally by a hardware processor(s) 308 of a computing device 310 executing code instructions 312A and/or training code 312B stored in a memory 312.

System 300 includes an endoscopic surgical system 314 that includes a user control mechanism 316, surgical controller 302, and endoscopic tool(s) 304. User control 316 is located outside the body of the patient and used by the operator for manipulation of endoscopic tool(s) 304 located inside the body of the patient. User control 316 may include, for example, one or more joysticks, one or more handles, and/or one or more mechanism arms. User control 316 may include a haptic device that applies a variable resistance to manipulations by the user, for example, a handle that may applying varying degrees of resistance to manipulations in different directions performed by the user. Manipulations performed by the user via user control 316 are received by surgical controller 302 that translates the manipulations into instructions for manipulation of endoscopic tool(s) 304. Endoscopic tool(s) 304 may include, for example, one or more robotic arms, optionally flexible and/or segmented, scissors, knives, ablation devices, probes, camera(s), and/or suturing equipment.

Additional details of an exemplary endoscopic surgical system 314 may be found, for example, with reference to United States Patent Application Publication No. US2017/0119483, by common inventors of the present application, and assigned to the same assignee as the present application, the contents of which are incorporated herein in their entirely.

System 300 may include code instructions 312B for training classifier(s) 306. Training code 312B may be stored in memory 312 and/or a data storage device 318. Alternatively, classifier(s) 306 is trained by another computing device (e.g., server 320) and transmitted to computing device 310 over a network 322 and/or remotely accessed by computing device 310 over network 322 (e.g., via a software interface for example, application programming interface (API), and/or software development kit (SDK)).

Multiple architectures of system 300 based on computing device 310 may be implemented. For example, computing device 310 may be integrated with surgical controller 302, for example, code 312A is stored on a memory of surgical controller 302 for execution by one or more hardware processors of surgical controller 302. In another implementation, computing device 310 may be implemented as a dedicated device in communication with surgical controller 302, for example, via a cable, a short range network, and/or network 322. In another exemplary implementation, computing device 310 may be implemented as one or more servers (e.g., network server, web server, a computing cloud, a virtual server) that provides remote services to one or more client terminals 324 over network 322, where each client terminal 324 is locally in communication with and/or is integrated with a respective endoscopic system.

Computing device 310 may be implemented as, for example, code executing on surgical controller 302, a client terminal, a server, a computing cloud, a virtual machine, a mobile device, a desktop computer, a thin client, a Smartphone, a Tablet computer, a laptop computer, a wearable computer, glasses computer, and a watch computer.

Computing device 310 is in communication with one or more sensors 326 that sense the instruction for manipulation of endoscopic tool(s) 304. Exemplary sensor(s) 326 are described below in additional detail. Sensor(s) 326 may be integrated within surgical controller 302, and/or in communication with surgical controller 302.

Hardware processor(s) 308 may be implemented, for example, as a central processing unit(s) (CPU), a graphics processing unit(s) (GPU), field programmable gate array(s) (FPGA), digital signal processor(s) (DSP), and/or application specific integrated circuit(s) (ASIC). Processor(s) 308 may include one or more processors (homogenous or heterogeneous), which may be arranged for parallel processing, as clusters and/or as one or more multi core processors.

Memory 312 stores code instructions 312A and/or 312B executable by processor(s) 308. Memory 312 may be implemented as, for example, a random access memory (RAM), read-only memory (ROM), and/or a storage device, for example, non-volatile memory, magnetic media, semiconductor memory devices, hard drive, removable storage, and optical media (e.g., DVD, CD-ROM).

Optionally, computing device 310 includes and/or is in communication with a data storage device 318 for example, for storing classifier 306. Data storage device 318 may be implemented as, for example, a memory, a local hard-drive, a removable storage device, an optical disk, a storage device, and/or as a remote server and/or computing cloud (e.g., accessed using a network connection). It is noted that code stored in data storage device 318 may be loaded into memory 312 for execution by processor(s) 308.

Optionally, computing device 310 is in communication with a user interface 328. User interface 328 may include a mechanism for the user to enter data (e.g., procedure type) and/or view data (e.g., an image of the computed envelope), for example, a touch screen, a display, a mouse, a keyboard, and/or a microphone with voice recognition software. User interface 328 may include a graphical user interface (GUI) presented on a display.

Network 322 may be implemented as, for example, the internet, a local area network, a virtual network, a wireless network, a cellular network, a local bus, a point to point link (e.g., wired), and/or combinations of the aforementioned.

Referring now back to FIG. 1, at 102, one or more classifiers 306 are trained, for example, as described with reference to FIG. 2. The classifiers are trained based on procedure performed by other physicians, in advance of the current procedure being performed.

Optionally, the classifier(s) is implemented as dynamic classifier that computes dynamic adaptations of the volume over the time interval. The dynamic classifier may compute the envelope in 4 dimensions, for example, adaptations of the volume of the envelope over a future time interval, which may originate from a current time. The dynamic classifier may be implemented as a Markov chain. The Markov chain may be used to represent a dynamic model of the endoscopic tool in the space of candidate manipulations.

At 104, one or more additional profiles are created and/or selected. The one or more additional profiles represent additional data that is fed into the classifier(s) with the goal of improving the relevancy and/or accuracy of the computed envelope. The additional profiles may provide personalization of the envelope according to the patient being treated, the endoscopic hardware being used, and/or the procedure being performed. Alternatively or additionally, the one or more additional profiles are used to select a certain classifier from a set of classifiers. Each classifier of the set of classifiers is trained based on different procedures, based on different endoscopic hardware, and/or based on different patient characteristics.

Optionally, a profile of the target individual is obtained and fed into the classifier in association with the indication of instructions for manipulation of the endoscopic tool for classifying the envelope. Alternatively or additionally a classifier is selected according to the profile. The classifier is selected and/or performs the classification according to an analysis of profiles of other patients correlated with the profile of the target individual. The profile of the target individual may be stored within the electronic medical record (EMR) of the patient, and/or within another dataset. Exemplary parameters stored in the profile of the target individual and the profiles of other patients include: gender, age, weight, body mass index (BMI), previous surgeries, anatomical variations, and medical history. The profile is used to compute the envelope according to other patients that are similar to the target individual. It is assumed that improved, more accuracy, and/or more relevant results are obtained when the envelope is computed based on manipulations of endoscopic tools performed for other similar patients.

Alternatively or additionally, a hardware profile of the endoscopic tool is obtained and fed into the classifier in association with the indication of instructions for manipulation of the endoscopic tool for classifying the envelope. The hardware profile may be manually entered by the operator (e.g., via a GUI and/or other interface) and/or automatically extracted (e.g., by querying the endoscopic device via an interface and/or from a dataset storing hardware data of endoscopic devices). Alternatively or additionally a classifier is selected according to the hardware profile. The classifier is selected and/or performs the classification of the envelope according to an analysis of hardware profiles of endoscopic tools used during other endoscopic medical procedures correlated with the hardware profile. Exemplary parameters stored in the hardware profile of the endoscopic tool used in the current procedure and the hardware profiles of endoscopic tools used during other endoscopic medical procedures include: tool manufacturer, tool model, tool intended use, length of tool, range of movement, range of force application, and tool architecture. It is assumed that improved, more accuracy, and/or more relevant results are obtained when the envelope is computed based on manipulations of similar endoscopic tools.

Alternatively or additionally, a procedure profile of the endoscopic procedure is obtained and fed into the classifier in association with the indication of instructions for manipulation of the endoscopic tool for classifying the envelope. The procedure profile may be manually entered by the user, for example, selection of the procedure from a list of defined procedure, and/or automatically extracted by code for example from a procedure billing code stored in the patient EMR. Alternatively or additionally a classifier is selected according to the procedure profile. The classifier is selected and/or performs the classification of the envelope according to an analysis of procedure profiles of other endoscopic medical procedures correlated with the procedure profile of the current procedure. Exemplary parameters stored in the procedure profile of the endoscopic procedure and the procedure profiles of other endoscopic procedures include: type of endoscopic procedure, planned route of endoscopic procedure, location of access port(s) into the body of the target individual. It is assumed that improved, more accuracy, and/or more relevant results are obtained when the envelope is computed based on manipulations of during similar endoscopic procedures.

At 106, indication(s) of instructions for manipulation of the endoscopic tool 304 outputted by sensor(s) 316 are obtained and fed into the classifier(s) 306. The instructions for manipulation of endoscopic tool 304 are based on user manipulation of user control 316 (e.g., joystick, arms, handles), which are converted into instructions for manipulation of endoscopic tool(s) 304 by surgical controller 302.

Optionally, a current (i.e., initial) position and orientation of the endoscopic tool is obtained, for example, from the endoscopic controllers. The position and/or orientation of the endoscopic tool may be stored, for example, as a vector, as a set of values of parameters, and/or as a set of instructions. The position and/or orientation of the endoscopic tool may be fed into the classifier in association with the instructions for manipulation of the endoscopic tool, for example, where the instructions for manipulation of the endoscopic tool are relative to the current position and/or orientation of the endoscopic tool.

Exemplary instructions for manipulation include adjustment of an angle of movement at a certain joint of the endoscopic tool, in-out motion relative to an insertion port, and/or a movement from a current position of the endoscopic tool. The movement at the joint may be adjustment of a rigid angle, and/or curvature of a flexible robotic arm at the "joint".

The indication(s) of instructions for manipulation of the endoscopic tool 304 outputted by sensor(s) 316 may be the electrical signal instructions and/or code instructions that are generated by surgical controller 302 for controlling endoscopic tool(s) 304. Sensor(s) 316 may be integrated with surgical controller 302. Alternatively or additionally, indication(s) of instructions for manipulation of the endoscopic tool 304 outputted by sensor(s) 316 are based on other measurements.

Optionally, sensor(s) 306 may include a computing device (e.g., surgical controller 302) that monitors activation of motors that control the endoscopic tool. For example, sensor(s) 306 may include a physical and/or virtual interface (e.g., sniffer) that senses code instructions and/or other signals for activation of the motors.

Sensor(s) 306 may include a current and/or voltage measuring sensor that senses voltage and/or current flowing through the motor(s) that control the endoscopic tool. The voltage and/or current is indicative of stress and/or torque experienced by the endoscopic tool during manipulation.

Surgical controller 302 may include the sensor 306 that receives manipulation instructions from a haptic device implementation of user control 316 manipulated by a user for activating the motor(s) that controls the endoscopic tool. For example, sensor(s) 306 may include a physical and/or virtual interface between user control 316 and surgical controller 302 and/or between user control 316 and endoscopic tool(s) 304.

The indications for instructions of manipulation of the endoscopic tool may be classified by the classifier in addition to additional data collected by additional sensors and/or the surgical controller, for example, a current location and/or position of the endoscopic tool(s), and a history of previous manipulations and/or previous locations of the endoscopic tool(s). The additional data may improve the accuracy of the classifier in computing the envelope.

At 108, the indication of instructions for manipulation of the endoscopic tool(s) is classified by the classifier(s) into an envelope. The envelope defines a volume that restricts manipulation of the endoscopic tool therein. Regions outside of the envelope represent unsafe manipulation that may lead to injury of the patient and/or inefficient manipulations that make performing the procedure difficult. Manipulations external to the envelope may be prohibited.

The classifier classifies the envelope based on previously obtained indications of instructions for manipulation of endoscopic tools during other endoscopic medical procedures performed in intrabody cavities of other patients, optionally in other similar patients, other similar procedures, and/or other similar endoscopic tool hardware, according to the selected profiles. Conceptually, the envelope represents the best practice manipulations performed by other physicians. Regions external to the envelope represent a zone where the beset practice manipulations were not performed by other physicians.

Optionally, the volume defined by the envelope is computed according to a threshold of the previously obtained indications of instructions for manipulation of endoscopic tools during other endoscopic medical procedures performed in intrabody cavities of other patients. The threshold differentiates between common manipulations indicative of allowed manipulations and uncommon manipulations indicative of prohibited manipulations. The threshold may be selected, for example, as a preset value, for example, the lower 10%, or 20% of outlier manipulations, representing the most extreme manipulations.

The envelope is computed to place the outlier manipulations externally to the envelope and the other manipulations within the volume of the envelope. Alternatively or additionally, the threshold may be based on manual indications provided by operators during training of the classifier. For example, when an operator detects an error in manipulation, the manipulation may be marked by the operator as a prohibited manipulation, for example, by pressing an icon within a GUI. The envelope is computed to place the prohibited manipulations outside the volume of the envelope.

Optionally, the envelope includes multiple nested sub-volumes of sub-envelops, where each sub-volume of each sub-envelope is located within another sub-volume of another sub-envelope. Each respective nested sub-volume represents a respective proportion according to a respective threshold of the previously obtained indications of instructions for manipulation of endoscopic tools during other endoscopic medical procedures performed in intrabody cavities of other patients. The sub-envelopes located close to the endoscopic tool represent safer and/or more efficiency manipulation sub-volumes. Sub-envelopes located further away from the endoscopic tools, and which include one or more sub-envelops within their respective sub-volumes represent less safe and/or less efficiency sub-volumes for manipulation. Optionally, the respective proportion of the respective nested sub-volume is indicative of a probability of manipulations being allowed within the respective nested sub-volume.

For example, the most inner sub-envelope represents a sub-volume that includes 100% of manipulations performed during the classifier training, the next inner sub-envelope represents a sub-volume that includes 90% of manipulations performed during the classifier training, and so on, where each envelope represents a decreasing 10% of manipulations. The final envelope may represent a volume that includes 20% of the manipulations. The zone external to the most outer envelope may represent a zone where only 20% of manipulations have been performed, representing a less safe and/or less efficient region.

Optionally, each of the different indications associated with the next sub-volumes represents inappropriate manipulations. Each indication may be generated according to an analysis indicative of a distance from the respective sub-envelope to the endoscopic tool when manipulated according to the instructions for manipulation. For example, the most inner sub-envelope represents a distance of 5 centimeters from the surface of the endoscopic tool to the first sub-envelope, and the second inner sub-envelope represents a distance of 10 centimeters from the surface of the endoscopic tool to the second sub-envelope.

Optionally, the different indications of inappropriate manipulations are indicative of increasing risk of injury to the patient when the endoscopic tool is manipulated within the respective sub-volume. For example, manipulation within the most inner sub-envelope represents an estimated risk of patient injury of about 1%, manipulation within the next sub-envelope represents an estimated risk of patient injury of about 2%, and so on until the most outer sub-envelope which represents the maximum tolerable risk of injury to the patient, for example, 7%, or 10%.

Alternatively or additionally, the envelope includes a probability density cloud. Sub-volumes of the envelope are each associated with a respective probability value indicative of manipulations being allowed within the respective sub-volume. Each probability is computed according to a ratio between previously performed manipulations within the sub-volume and total performed manipulations. For example, regions within the probability cloud of the envelope close to the surface of the endoscopic tool may represent regions that include 100% of previously performed manipulations. Regions within the probability cloud of the envelope further away from the surface of the endoscopic tool may represent regions that include relatively reduced probabilities, since fewer and fewer extreme manipulations to movements far away are likely to have been performed.

Optionally, the envelope includes multiple sub-envelopes each defining restriction of movement of a respective independently bendable flexible section of the endoscopic tool.

Optionally, an indication of the envelope is marked on an image presented on a display (e.g., user interface 328). The image may be a visual image of the operating field captured by a video camera located within the intrabody cavity of the target individual, an anatomical and/or virtual image captured by an anatomical imaging modality imaging the target individual (e.g., generated from ultrasound, MRI, and/or CT images), and/or an anatomical and/or virtual image generated from an anatomical image obtained from an atlas and/or rendered from data collected from other patients. The indication of the envelope may be rendered and presented on the image, for example, using a distinct color. The visual representation of the envelope marked on the image may assist the user in planning the manipulations of the tools, by indicating the zones outside of the envelope where manipulations are prohibited.

At 110, the indication of instructions for manipulation of the endoscopic tool is analyzed according to the envelope to determine when the instructions are for manipulation of the endoscopic tool externally to the envelope.

Optionally, the marking of the envelope presented on the image on the display dynamically changes colors according to a distance between a current location of the endoscopic tool and the envelope. The color dynamically changes according to a real time value of the distance. For example, a value representing a relatively far distance between the current location of the endoscopic tool and the envelope (e.g., 20 centimeters) triggers depiction of the envelope as green indicating a relatively safe and/or large volume for manipulation therein. When the distance decreases to a relatively short distance (e.g., 5 centimeters), the color of the envelope is shown in red, indicating a relatively small volume for safe manipulation therein.

Optionally, when the indication of inappropriate manipulation is detected, a marking denoting the inappropriate manipulation is generated. For example, a beep sound is generated, a message is presented on the display, and/or an icon is shown indicating the manipulation is inappropriate.

Optionally, when the indication of inappropriate manipulation is detected, a recommendation for an alternative manipulation that remains within the volume defined by the envelope is computed. The alternative manipulation may be computed in comparison to the instructions for manipulation of the endoscopic tool according to one or more of: a predicted reduction in strain within the endoscopic tool, a predicted reduction in radius of curvature of a portion of the endoscopic tool, and/or a predicted reduction in distance to tissue located externally to the envelope. For example, the alternative manipulation is computed as an alternative angle, for example, by subtracting 180 degrees for the current bending angle. For example, a dissection may be performed at a certain bending angle of the endoscopic tool, or at the certain bending angle—180 degrees, which represents a different dissection direction, such as top to bottom vs. bottom to top. The envelope may be computed according to the safer dissection direction (i.e., downwards or upwards), preventing the operator from dissecting in the unsafe direction and/or guiding the operator to dissect in the safe direction.

Optionally, the instructions for manipulation of the endoscopic tool are analyzed to identify an ergonomically poor posture of the operator. For example, the classifier may output an indication that the classified envelope corresponds to ergonomically poor posture of the operator performing the manipulation, and/or the envelope may represent manipulations performed with ergonomically easy posture where manipulations outside the envelope represent manipulations performed with ergonomically poor posture. The classifier may be trained to detect the ergonomically poor posture of the operator based on manipulations labeled as associated with ergonomically poor posture or ergonomically easy posture. Such classifier may compute an envelope denoting a volume encompassing manipulations performed with ergonomically easy posture. Manipulations outside the envelope denote ergonomically poor posture.

At 112, the surgical controller is provided with an indication of inappropriate manipulation according to the analysis. For example, code instructions are transmitted from computing device 310 to surgical controller 302 indicating that the manual manipulation of user control 316 by the user translate into inappropriate manipulations of endoscopic tool(s) 304.

The surgical controller is provided with the indication of inappropriate manipulation prior to the surgical controller activating the endoscopic tool for implementing the instructions for manipulation of the endoscopic tool. The surgical controller may prevent or reduce injury to the patient from inappropriate manipulations of the endoscopic tool outside of the envelope, even when the operator attempts such inappropriate manipulations.

Optionally, manipulations performed by the user manipulating user control 316 are analyzed with the indication of inappropriate manipulation provided to surgical controller 302 prior to translation into instructions for manipulation of endoscopic tool(s) 304. The analysis may be associated with a processing delay, which may be insignificant to the operator performing the procedure. The delay enables surgical controller 302 to block prohibited manipulations performed by the user using user control 316 into dangerous and/or inefficient manipulations of endoscopic tool(s) 304, for example, manipulations that would otherwise move the endoscopic tool(s) 304 out of the envelope.

Optionally, haptic feedback is provided to a haptic device implementation of user control 316 manipulated by the user for manipulating the endoscopic tool. The haptic feedback is generated according to the indication of inappropriate manipulation. The haptic feedback may be provided and/or generated by surgical controller 302 and/or computing device 310. The haptic feedback may include instructions for resistance to movement of the haptic device when the haptic device is manipulated for manipulation of the endoscopic tool externally to the envelope. The amount of resistance may be proportional to the risk of injury and/or inefficiency of manipulation defined by the envelope, for example, the sub-volumes and/or probability cloud. Alternatively or additionally, the amount of resistance is proportional to a vector (i.e., distance and/or direction) from a current position (e.g., pose, in 3D coordinates and/or 6 degrees of freedom) of the endoscopic tool to the envelope. The distance may be to the boundary of the envelope, and/or to a predefined position within the envelope denoting adequate and/or optimal location (e.g., when the envelope is represented as a probability cloud). The metric for the vector and/or distance may be based on the Ferenet-Serret parameters for spatial curves. Alternatively or additionally, manipulation externally to the envelope is blocked by a full resistance to prevent such manipulations. For example, the user is prevented from moving the joystick and/or handles in a direction that would otherwise cause the endoscopic tool(s) to move outside of the envelope by increased resistance in the direction such that the user is unable to further move the joystick and/or handle.

At 114, acts 106-112 are dynamically iterated during the procedure. The envelope is dynamically classified by the classifier as the instructions for manipulation of the endoscopic tool are dynamically outputted by the sensor(s) during the endoscopic procedure. The surgical controller is provided with the relevant indication(s) of inappropriate manipulation during the procedure. The dynamic iterations guide the user into manipulating the endoscopic tools within the dynamically computed envelopes, reducing risk of injury to the patient during the procedure, and/or increasing efficiency of movement of the endoscopic tool(s) during the procedure.

Referring now back to FIG. 2, at 202, one or more profiles may be obtained and/or created for each endoscopic procedure. The profiles are as described with reference to act 104 of FIG. 1.

At 204, indication(s) of instructions for manipulation of the endoscopic tool outputted by sensor(s) are obtained for each endoscopic procedure. Optionally, the indications of instructions for manipulation are dynamically obtained during the procedure. The indications may be stored sequentially, defining a relationship between earlier and later indications. The indication(s) of instructions for manipulation of the endoscopic tool outputted by sensor(s) are obtained as described with reference to act 106 of FIG. 1.

At 206, one or more prohibited indications each of prohibited manipulations of the respective endoscopic tool may be obtained. For example, the operator may manually indicate that the previously performed manipulation was prohibited, and performed in error. For example, the operator may press on an icon, and/or say key words into a speaker which are analyzed by speech analysis code.

Alternatively or additionally, the operator may manually assign a category and/or value to one or more manipulations indicating a degree of safety and/or efficiency of the manipulation. For example, a probability value, a value from 1-10, or select from available categories.

At 208, multiple training envelopes are computed according to the indication of instructions for manipulation of the endoscopic tool for each procedure. Each training envelope may be computed according to one or more sets of instructions. For example, the envelope may be computed according to the volume encompassed by multiple manipulations performed over each sequential 5 minute time interval of the procedure. Each envelope defines a volume that restricts movement of the endoscopic tools therein.

When prohibited indications are provided, and/or varying categories are assigned to the manipulations, the training envelopes are computed accordingly. For example, the volumes of the training envelopes exclude the prohibited manipulations. The training envelop is computed such that the prohibited manipulates are located externally to the training envelope.

Optionally, each one of the training envelopes is computed for a certain position and/or orientation of the endoscopic tool. The position and/or orientation may be defined by a set of parameters of the surgical controller. For example, a robotic arm that is advanced 10 centimeters into the body at a defined insertion direction where the most distal segment of the arm is flexed at 45 degrees and rotated by 60 degrees to the midline of the patient may be stored as a vector, as a set of parameters that defined the position and/or orientation, and/or a set of values of parameters for controlling the motors. The position and/or orientation may be according to a defined coordinate system (e.g., Cartesian) with optional values for pitch, roll, and yaw. The position and/or orientation of the endoscopic tool may be stored as a set of parameters that are used to return to the endoscopic tool to the same position and/or orientation.

Each one of the training envelopes may be computed for each possible position and/or orientation of the endoscopic tool according to a resolution, for example, a range of +/−1 centimeter for distance and/or +/−5 degrees for angles.

Each training envelop may be computed according to a volume (and/or surface that encompasses the volume) that encompasses manipulations performed during other procedures, where the manipulations are relative to (i.e., initiated from) the certain position and/or orientation. For example, one envelope is created for the endoscopic located at certain position and orientation based manipulations performed by other operators during other endoscopic procedures starting from the same position and orientation. For example, some operators moved the endoscopic tool forward 5 centimeters, other moved the endoscopic tool forward 7 centimeters, others moved the endoscopic tool forward 10 centimeters, others angled the endoscopic tool up by 30 degrees, and others angled the endoscopic tool up by 45 degrees. The envelope may be computed to include the volume encompassed by the forward movement of 7-10 centimeters and the up angulations of 30-45 degrees.

Optionally, outlier manipulations satisfying outlier criteria are excluded for computation of the respective envelope. The outlier criteria may include for example, a certain percentage of the most extreme manipulations, and/or the set of manipulations that are significantly different than the rest of the manipulations. For example, referring to the example in the previous paragraph, a manipulation in a reverse direction and/or manipulation in a downward angle is excluded from computation of the envelope.

At 210, one classifier or more classifiers are trained according to the computed training envelopes, and the indication(s) of instructions for manipulation of the endoscopic tool(s). The classifier(s) is trained to classify a new envelope for a new indication of instructions for manipulation of an endoscopic tool during a new endoscopic procedure.

Optionally, multiple classifiers are generated. Each classifier is generated by aggregating the computed training envelopes and the indication(s) of instructions for manipulation of the endoscopic tool(s) according to respective profiles, for example, based on common patient characteristics, and/or based on common endoscopic hardware, and/or based on common endoscopic procedures.

At 212, the classifier(s) 306 are stored on server 320 and/or made accessible to remotely located computing devices 310 (e.g., downloaded to the respective computing devices and/or providing remote access such as via an interface (e.g., API)).

At 214, acts 202-212 are iterated when new procedures are performed, for updating the classifier(s).

Figure 4:
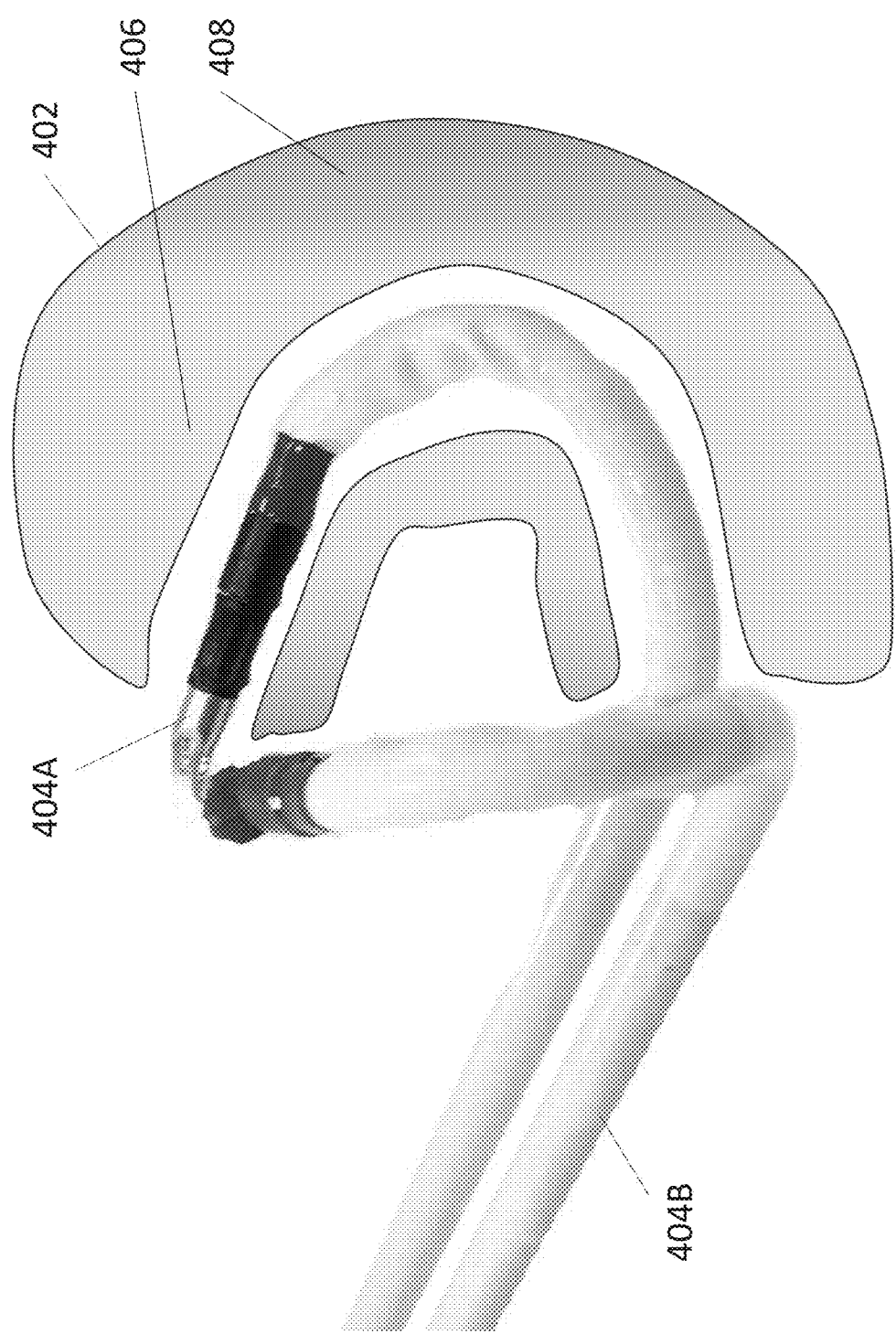
FIG. 4, which is a schematic depicting an example of an envelope 402 defining a volume that restricts therein manipulation of an endoscopic tool 404A, in accordance with some embodiments of the present invention.

Reference is now made to FIG. 4, which is a schematic depicting an example of an envelope 402 defining a volume that restricts therein manipulation of an endoscopic tool 404A, in accordance with some embodiments of the present invention. Envelope 402 is computed by classifier(s) based on an input of indication of instructions for manipulation of the endoscopic tool 404A outputted by sensor(s), as described herein. Envelope 402 may be defined as a probability density cloud, shown as a gradient, where for example, portions of the envelope closer to the tool 408 are shown with lighter texture (e.g., less density of points, lighter pixel values), optionally indicating decreased probability of inappropriate manipulation, and portions of the envelope farther away from the tool 410 are shown with darker texture (e.g., greater density points, darker pixel values), optionally indicating increased probability of inappropriate manipulation, as described herein. The feedback provided to the haptic device may be computed according to a vector and/or distance from tool 404A to envelope 402, optionally to defined thresholds (e.g., probability thresholds) within the probability cloud of envelope 402, as described herein.

When multiple endoscopic tools are being independently manipulated, a respective envelope may be computed for each tool. Another endoscopic tool 404B is shown without its envelope, for clarity. Tools 404A and 404B may be independently manipulated. Another envelope may be computed for endoscopic tool 404B, in a similar manner of computing envelope 402 for tool 404A.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant endoscopic tools will be developed and the scope of the term endoscopic tool is intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A computer implemented method of providing a surgical controller with instructions to restrict a manipulation of an endoscopic tool during an endoscopic medical procedure in an intrabody cavity, comprising:

inputting into at least one classifier, at least one indication of instructions for manipulation of the endoscopic tool outputted by at least one sensor;

classifying by the at least one classifier, the at least one indication of instructions into an envelope defining a volume that restricts therein manipulation of the endoscopic tool, wherein the at least one classifier classifies the envelope based on previously obtained indications of instructions for manipulation of endoscopic tools during other endoscopic medical procedures performed in intrabody cavities of other patients;

analyzing the at least one indication of instructions for manipulation of the endoscopic tool according to the envelope to determine when the instructions are for manipulation of the endoscopic tool externally to the envelope; and providing the surgical controller with an indication of inappropriate manipulation according to the analysis.

2. The method of claim 1, wherein the endoscopic procedure is performed by introducing the endoscopic tool into an abdominal cavity of a patient via transvaginal access.

3. The method of claim 1, wherein the envelope is defined in four dimensions, the method including dynamically defining the volume over a time interval.

4. The method of claim 3, wherein the at least one classifier comprises a dynamic classifier that computes dynamic adaptations of the volume over the time interval.

5. The method of claim 4, wherein the dynamic classifier is implemented as a Markov Chain.

6. The method of claim 1, wherein the envelope is dynamically classified by the at least one classifier as the instructions for manipulation of the endoscopic tool are dynamically outputted by the at least one sensor during the endoscopic procedure.

7. The method of claim 1, further comprising providing haptic feedback to a haptic device manipulated by a user for manipulating the endoscopic tool, the haptic feedback generated according to the indication of inappropriate manipulation.

8. The method of claim 7, wherein the haptic feedback comprises resistance to movement of the haptic device when the haptic device is manipulated for manipulation of the endoscopic tool externally to the envelope.

9. The method of claim 1, further comprising providing haptic feedback to a haptic device manipulated by a user for manipulating the endoscopic tool, the haptic feedback comprising a resistance force proportional to a vector from a current position of the endoscopic tool to the envelope.

10. The method of claim 1, wherein the envelope is classified according to the instructions for manipulation of the endoscopic tool relative to an initial position and orientation of the endoscopic tool.

11. The method of claim 1, wherein the envelope is classified according to a history of previous manipulations of the endoscopic tool.

12. The method of claim 1, wherein the surgical controller is provided with the indication of inappropriate manipulation prior to the surgical controller activating the endoscopic tool for implementing the instructions for manipulation of the endoscopic tool.

13. The method of claim 1, wherein the volume defined by the envelope is computed according to a threshold of the previously obtained indications of instructions for manipulation of endoscopic tools during other endoscopic medical procedures performed in intrabody cavities of other patients.

14. The method of claim 13, wherein the threshold differentiates between common manipulations indicative of allowed manipulations and uncommon manipulations indicative of prohibited manipulations.

15. The method of claim 1, wherein the envelope comprises a plurality of nested sub-volumes, each respective nested sub-volume indicative of a respective proportion according to a respective threshold of the previously obtained indications of instructions for manipulation of endoscopic tools during other endoscopic medical procedures performed in intrabody cavities of other patients.

16. The method of claim 15, wherein the respective proportion of the respective nested sub-volume is indicative of a probability of manipulations being allowed within the respective nested sub-volume.

17. The method of claim 15, wherein each of a plurality of different indications of inappropriate manipulations is generated according to an analysis indicative of a distance from the envelope to the endoscopic tool when manipulated according to the instructions for manipulation.

18. The method according to claim 17, wherein the plurality of different indications of inappropriate manipulations are indicative of increasing risk of injury to the patient when the endoscopic tool is manipulated within the respective sub-volume.

19. The method of claim 1, wherein the envelope comprises a probability density cloud, wherein sub-volumes of the envelope are each associated with a respective probability value indicative of manipulations being allowed within the respective sub-volume, wherein each probability is computed according to a ratio between previously performed manipulations within the sub-volume and total performed manipulations.

20. The method of claim 1, wherein the envelope comprises a plurality of sub-envelopes each defining restriction of movement of a respective independently bendable flexible section of the endoscopic tool.

21. The method of claim 1, wherein an indication of the envelope is marked on an image presented on a display, wherein the image is at least one of: captured by a video camera located within a target individual, captured by an anatomical imaging modality imaging the target individual, and an anatomical image obtained from an atlas.

22. The method of claim 21, wherein the envelope dynamically changes colors according to a distance between a current location of the endoscopic tool and the envelope, the color indicative of the amount of the distance.

23. The method of claim 1, wherein the indication of inappropriate manipulation is presented on a display.

24. The method of claim 1, further comprising receiving a profile of a target individual and classifying the envelope by the at least one classifier according to an analysis of profiles of other patients correlated with the profile of the target individual.

25. The method of claim 24, wherein the profile of the target individual and the profiles of other patients include at least one parameter selected from the group consisting of: gender, age, weight, body mass index (BMI), previous surgeries, anatomical variations, and medical history.

26. The method of claim 1, further comprising receiving a hardware profile of the endoscopic tool and classifying the envelope by the at least one classifier according to an analysis of hardware profiles of endoscopic tools used during other endoscopic medical procedures correlated with the hardware profile.

27. The method of claim 26, wherein the hardware profile of the endoscopic tool and the hardware profiles of endoscopic tools used during other endoscopic medical procedures include at least one parameter selected from the group consisting of: tool manufacturer, tool model, tool intended use, length of tool, range of movement, range of force application, and tool architecture.

28. The method of claim 1, further comprising receiving a procedure profile of the endoscopic procedure and classifying the envelope by the at least one classifier according to an analysis of procedure profiles of other endoscopic procedures correlated with the procedure profile.

29. The method of claim 28, wherein the procedure profile of the endoscopic procedure and the procedure profiles of other endoscopic procedures include at least one parameter selected from the group consisting of: type of endoscopic procedure, planned route of endoscopic procedure, and location of access port(s) into the body of the target individual.

30. The method of claim 1, wherein the surgical controller comprises the at least one sensor and the at least one sensor receives manipulation instructions from a haptic device manipulated by a user for activating at least one motor that controls the endoscopic tool.

31. The method of claim 1, wherein the at least one sensor comprises a computing device that monitors activation of motors that control the endoscopic tool.

32. The method of claim 1, wherein the at least one sensor comprises a current measuring sensor that senses current flowing through at least one motor that controls the endoscopic tool, wherein the current is indicative of at least one of stress and torque experienced by the endoscopic tool during manipulation.

33. The method of claim 1, wherein the instructions for manipulation include a movement from a current position of the endoscopic tool.

34. The method of claim 1, further comprising computing a recommendation for an alternative manipulation that remains within the volume defined by the envelope.

35. The method of claim 34, wherein the alternative manipulation is computed in comparison to the instructions for manipulation of the endoscopic tool according to at least one of: a predicted reduction in strain within the endoscopic tool, a predicted reduction in radius of curvature of a portion of the endoscopic tool, and a predicted reduction in distance to tissue located externally to the envelope.

36. The method of claim 34, further comprising analyzing the instructions for manipulation of the endoscopic tool to identify an ergonomically poor posture of the operator, and wherein the alternative manipulation is computed according to manipulation of the endoscopic tool based on an ergonomic easing of the operator.

37. The method of claim 34, wherein the alternative manipulation is computed as an alternative angle for performing a dissection using the endoscopic tool.

38. The method of claim 37, wherein the alternative manipulation is computed by subtracting 180 degrees from a current bending angle of the endoscopic tool.

39. The method of claim 1, wherein the at least one classifier is trained according to endoscopic procedures performed by operators instructed for ergonomically easy manipulation of the endoscopic tool, wherein the envelope denotes a volume including possible ergonomically easy manipulations.

40. The method of claim 1, wherein the instructions for manipulation include at least one of: angle of movement at a joint, and in-out motion relative to an insertion port.

41. A computer implemented method of training at least one classifier to classify an indication of instructions for manipulation of an endoscopic tool during an endoscopic medical procedure in an intrabody cavity, the method comprising:
receiving for each of a plurality of endoscopic procedures, at least one indication of instructions for manipulation of the endoscopic tool outputted by at least one sensor;
computing a plurality of training envelopes according to the at least one indication of instructions for manipulation of the endoscopic tool for the plurality of endoscopic procedures, wherein each training envelope of the plurality of training envelopes defines a respective volume denoting restricted manipulation of the endoscopic tool therein; and
training at least one classifier according to the plurality of training envelopes and the at least one indication of instructions for manipulation of the endoscopic tool, to classify a new envelope for a new indication of instructions for manipulation of an endoscopic tool during a new endoscopic procedure.

42. The method of claim 41, wherein each one of the plurality of training envelopes is computed for a certain position and orientation of the endoscopic tool according to a volume that encompasses a plurality of manipulations performed relative to the certain position and orientation during the plurality of endoscopic procedures.

43. The method of claim 42, wherein outlier manipulations of the plurality of manipulations satisfying outlier criteria are excluded for computation of the respective envelope.

44. The method of claim 41, further comprising:
receiving a plurality of prohibited indications each of a prohibited manipulation of the respective endoscopic tool, wherein the plurality of training envelopes are computed according to the prohibited indications, wherein the volumes of the plurality of training envelopes exclude the prohibited manipulations and the prohibited manipulations are located externally to the plurality of envelopes.

45. A system for providing a surgical controller with instructions to restrict a manipulation of an endoscopic tool during an endoscopic medical procedure in an intrabody cavity, comprising:
a non-transitory memory having stored thereon a code for execution by at least one hardware processor, the code comprising:
code for inputting into at least one classifier, at least one indication of instructions for manipulation of the endoscopic tool outputted by at least one sensor;
code for classifying by the at least one classifier, the at least one indication of instructions into an envelope defining a volume that restricts therein manipulation of the endoscopic tool, wherein the at least one classifier classifies the envelope based on previously obtained indications of instructions for manipulation of endoscopic tools during other endoscopic medical procedures performed in intrabody cavities of other patients;
code for analyzing the at least one indication of instructions for manipulation of the endoscopic tool according to the envelope to determine when the instructions are for manipulation of the endoscopic tool externally to the envelope; and
code for providing the surgical controller with an indication of inappropriate manipulation according to the analysis.

* * * * *